US009399111B1

(12) United States Patent
Hanina

(10) Patent No.: US 9,399,111 B1
(45) Date of Patent: Jul. 26, 2016

(54) METHOD AND APPARATUS FOR EMOTIONAL BEHAVIOR THERAPY

(71) Applicant: Ai Cure Technologies, Inc., New York, NY (US)

(72) Inventor: Adam Hanina, New York, NY (US)

(73) Assignee: AIC Innovations Group, Inc., New York, NY (US)

( * ) Notice: Subject to any disclaimer, the term of this patent is extended or adjusted under 35 U.S.C. 154(b) by 459 days.

(21) Appl. No.: 13/841,642

(22) Filed: Mar. 15, 2013

(51) Int. Cl.
*A61M 21/00* (2006.01)
*A61M 21/02* (2006.01)

(52) U.S. Cl.
CPC ..................... *A61M 21/02* (2013.01)

(58) Field of Classification Search
CPC ............. A61M 21/00; A61M 2021/0044; A61M 2021/005; G06K 9/00221; G06K 9/00302; G09B 5/00
USPC ............. 600/26–28; 128/897–898; 348/77; 382/159
See application file for complete search history.

(56) References Cited

U.S. PATENT DOCUMENTS

| | | | |
|---|---|---|---|
| 3,814,845 | A | 6/1974 | Hurlbrink et al. |
| 5,065,447 | A | 11/1991 | Barnsley et al. |
| 5,441,047 | A | 8/1995 | David et al. |
| 5,544,649 | A | 8/1996 | David et al. |
| 5,619,991 | A | 4/1997 | Sloane |
| 5,646,912 | A | 7/1997 | Cousin |
| 5,752,621 | A | 5/1998 | Passamante |
| 5,764,296 | A | 6/1998 | Shin |
| 5,810,747 | A | 9/1998 | Brundy et al. |
| 5,911,132 | A | 6/1999 | Sloane |
| 5,961,446 | A | 10/1999 | Beller et al. |
| 6,151,521 | A | 11/2000 | Guo et al. |
| 6,154,558 | A | 11/2000 | Hsieh |
| 6,233,428 | B1 | 5/2001 | Fryer |
| 6,283,761 | B1 | 9/2001 | Joao |
| 6,380,858 | B1 | 4/2002 | Yarin et al. |
| 6,409,661 | B1 | 6/2002 | Murphy |
| 6,421,650 | B1 | 7/2002 | Goetz et al. |

(Continued)

OTHER PUBLICATIONS

Niebles et al., *Unsupervised Learning of Human Action Categories Using Spatial-Temporal Words,* Int. J. Compt. Vis, (Sep. 2008) (20 pages).
Ammouri, S.; Biloduau, G. -A, "Face and Hands Detection and Tracking Applied to the Monitoring of Medication Intake," Computer and Robot Vision, 2008. CRV '08. Canadian Conference, 147(154):28-30, May 2008.
Batz, et al. "A computer Vision System for Monitoring Medication Intake," in Proc. IEEE 2nd Canadian Conf. on Computer and Robot Vision, Victoria, BC, Canada, 2005, pp. 362-369.

(Continued)

*Primary Examiner* — John Lacyk
(74) *Attorney, Agent, or Firm* — Fish & Richardson P.C.

(57) ABSTRACT

A system and method for encouraging emotional behavior therapy. The method includes the steps of identifying a particular emotional behavior therapy prescription regimen to performed by a user, determining one or more procedures for administering such emotional behavior therapy prescription regimen and identifying one or more video activity sequences associated with such procedures. On a display one or more instruction prompts associated with the emotional behavior therapy administration are provided, and video activity sequences of actual administration following the one or more instruction prompts are captured by a video capture device. The captured video activity sequences are stored to a non-transitory computer readable storage medium and are compared the identified video activity sequences by a computer processor to determine differences therebetween. On the display an updated one or more further instruction prompts associated with the emotional behavior therapy administration are provided in response to the determined differences.

20 Claims, 3 Drawing Sheets

(56) References Cited

U.S. PATENT DOCUMENTS

| | | | |
|---|---|---|---|
| 6,483,993 B1 | 11/2002 | Misumi et al. | |
| 6,484,144 B2 | 11/2002 | Martin et al. | |
| 6,535,637 B1 | 3/2003 | Wootton et al. | |
| 6,611,206 B2 | 8/2003 | Eshelman et al. | |
| 6,705,991 B2 | 3/2004 | Bardy | |
| 6,879,970 B2 | 4/2005 | Shiffman et al. | |
| 6,988,075 B1 | 1/2006 | Hacker | |
| 7,184,047 B1 | 2/2007 | Crampton | |
| 7,184,075 B2 | 2/2007 | Reiffel | |
| 7,256,708 B2 | 8/2007 | Rosenfeld et al. | |
| 7,277,752 B2 | 10/2007 | Matos | |
| 7,304,228 B2 | 12/2007 | Bryden et al. | |
| 7,307,543 B2 | 12/2007 | Rosenfeld et al. | |
| 7,317,967 B2 | 1/2008 | DiGianfilippo et al. | |
| 7,340,077 B2 | 3/2008 | Gokturk | |
| 7,359,214 B2 | 4/2008 | Heard | |
| 7,395,214 B2 | 7/2008 | Shillingburg | |
| 7,415,447 B2 | 8/2008 | Shiffman et al. | |
| 7,448,544 B1 | 11/2008 | Louie et al. | |
| 7,562,121 B2 | 7/2009 | Berisford et al. | |
| 7,627,142 B2 | 12/2009 | Kurzweil et al. | |
| 7,657,443 B2 | 2/2010 | Crass et al. | |
| 7,692,625 B2 | 4/2010 | Morrison et al. | |
| 7,747,454 B2 | 6/2010 | Bartfeld et al. | |
| 7,761,311 B2 | 7/2010 | Clements et al. | |
| 7,769,465 B2 | 8/2010 | Matos | |
| 7,774,075 B2 | 8/2010 | Lin et al. | |
| 7,874,984 B2 | 1/2011 | Elsayed et al. | |
| 7,881,537 B2 | 2/2011 | Ma et al. | |
| 7,908,155 B2 | 3/2011 | Fuerst et al. | |
| 7,912,733 B2 | 3/2011 | Clements et al. | |
| 7,956,727 B2 | 6/2011 | Loncar | |
| 7,983,933 B2 | 7/2011 | Karkanias et al. | |
| 8,321,284 B2 | 11/2012 | Clements et al. | |
| 8,538,775 B2 | 9/2013 | Skomra | |
| 8,602,794 B2 * | 12/2013 | Cohen | 434/323 |
| 2001/0049673 A1 | 12/2001 | Dulong et al. | |
| 2001/0056358 A1 | 12/2001 | Dulong et al. | |
| 2002/0026330 A1 | 2/2002 | Klein | |
| 2002/0093429 A1 | 7/2002 | Matsushita et al. | |
| 2002/0143563 A1 | 10/2002 | Hufford et al. | |
| 2003/0164172 A1 | 9/2003 | Chumas et al. | |
| 2003/0190076 A1 | 10/2003 | Delean | |
| 2003/0225325 A1 | 12/2003 | Kagermeier et al. | |
| 2004/0100572 A1 | 5/2004 | Kim | |
| 2004/0107116 A1 | 6/2004 | Brown | |
| 2004/0155780 A1 | 8/2004 | Rapchak | |
| 2005/0144150 A1 | 6/2005 | Ramamurthy et al. | |
| 2005/0149361 A1 | 7/2005 | Saus et al. | |
| 2005/0180610 A1 | 8/2005 | Kato et al. | |
| 2005/0182664 A1 | 8/2005 | Abraham-Fuchs et al. | |
| 2005/0234381 A1 | 10/2005 | Niemetz et al. | |
| 2005/0267356 A1 | 12/2005 | Ramasubramanian et al. | |
| 2006/0066584 A1 | 3/2006 | Barkan | |
| 2006/0218011 A1 | 9/2006 | Walker et al. | |
| 2006/0238549 A1 | 10/2006 | Marks | |
| 2007/0008112 A1 | 1/2007 | Covannon et al. | |
| 2007/0008113 A1 | 1/2007 | Spoonhower et al. | |
| 2007/0030363 A1 | 2/2007 | Cheatle et al. | |
| 2007/0118389 A1 | 5/2007 | Shipon | |
| 2007/0194034 A1 | 8/2007 | Vasiadis | |
| 2007/0233035 A1 | 10/2007 | Wehba et al. | |
| 2007/0233049 A1 | 10/2007 | Wehba et al. | |
| 2007/0233050 A1 | 10/2007 | Wehba et al. | |
| 2007/0233281 A1 | 10/2007 | Wehba et al. | |
| 2007/0233520 A1 | 10/2007 | Wehba et al. | |
| 2007/0233521 A1 | 10/2007 | Wehba et al. | |
| 2007/0265880 A1 | 11/2007 | Bartfeld et al. | |
| 2007/0273504 A1 | 11/2007 | Tran | |
| 2008/0000979 A1 | 1/2008 | Poisner | |
| 2008/0012818 A1 | 1/2008 | Rodgers | |
| 2008/0093447 A1 | 4/2008 | Johnson et al. | |
| 2008/0114226 A1 | 5/2008 | Music et al. | |
| 2008/0114490 A1 | 5/2008 | Jean-Pierre | |
| 2008/0138604 A1 | 6/2008 | Kenney et al. | |
| 2008/0140444 A1 | 6/2008 | Karkanias et al. | |
| 2008/0162192 A1 | 7/2008 | Vonk et al. | |
| 2008/0178126 A1 | 7/2008 | Beeck et al. | |
| 2008/0201174 A1 | 8/2008 | Ramasubramanian et al. | |
| 2008/0219493 A1 | 9/2008 | Tadmor | |
| 2008/0275738 A1 | 11/2008 | Shillingburg | |
| 2008/0290168 A1 | 11/2008 | Sullivan et al. | |
| 2008/0297589 A1 | 12/2008 | Kurtz et al. | |
| 2008/0303638 A1 | 12/2008 | Nguyen et al. | |
| 2009/0018867 A1 | 1/2009 | Reiner | |
| 2009/0043610 A1 | 2/2009 | Nadas et al. | |
| 2009/0048871 A1 | 2/2009 | Skomra | |
| 2009/0095837 A1 | 4/2009 | Lindgren | |
| 2009/0127339 A1 | 5/2009 | Needham et al. | |
| 2009/0128330 A1 | 5/2009 | Monroe | |
| 2009/0159714 A1 | 6/2009 | Coyne, III et al. | |
| 2009/0217194 A1 | 8/2009 | Martin et al. | |
| 2009/0245655 A1 | 10/2009 | Matsuzaka | |
| 2010/0042430 A1 | 2/2010 | Bartfield | |
| 2010/0050134 A1 | 2/2010 | Clarkson | |
| 2010/0057646 A1 | 3/2010 | Martin et al. | |
| 2010/0092093 A1 | 4/2010 | Akatsuka et al. | |
| 2010/0136509 A1 | 6/2010 | Mejer et al. | |
| 2010/0138154 A1 | 6/2010 | Kon | |
| 2010/0255598 A1 | 10/2010 | Melker | |
| 2010/0262436 A1 | 10/2010 | Chen et al. | |
| 2010/0316979 A1 | 12/2010 | Von Bismarck | |
| 2011/0021952 A1 | 1/2011 | Vallone | |
| 2011/0119073 A1 | 5/2011 | Hanina et al. | |
| 2011/0141009 A1 | 6/2011 | Izumi | |
| 2011/0153360 A1 | 6/2011 | Haninia et al. | |
| 2011/0161109 A1 | 6/2011 | Pinsonneault et al. | |
| 2011/0195520 A1 | 8/2011 | Leider et al. | |
| 2011/0275051 A1 | 11/2011 | Hanina et al. | |
| 2012/0075464 A1 | 3/2012 | Derenne et al. | |
| 2013/0337421 A1 * | 12/2013 | Gerken, III | 434/236 |
| 2014/0016860 A1 * | 1/2014 | Senechal et al. | 382/159 |
| 2014/0278514 A1 * | 9/2014 | Stromberg | 705/2 |
| 2014/0370470 A1 * | 12/2014 | Aristizabal et al. | 434/236 |

OTHER PUBLICATIONS

Bilodeau et al. Monitoring of Medication Intake Using a Camera System. Journal of Medical Systems 2011. [retrieved on Feb. 18, 2013] Retrieved from ProQuest Technology Collection.

Chen, Pauline W., "Texting as a Health Tool for Teenagers", The New York Times, Nov. 5, 2009, http://www.nytimes.com/2009/11/05/health/0512/899,510 (3 pages).

Danya International, Inc., "Pilot Study Using Cell Phones for Mobile Direct Observation Treatment to Monitor Medication Compliance of TB Patients", Mar. 20, 2009, www.danya,com/MDOT.asp , (2 pages).

Global Tuberculosis Control: A short update to the 2009 report, World Health Organization, (2009) (48 pages).

Huynh et al., "Real time detection, tracking and recognition of medication intake." World Academy of Science, Engineering and Technology 60 (2009), 280-287.

Mintchell, "Exploring the Limits of Machine Vision", Automation World, Oct. 1, 2011 (6 pages).

Osterberg, Lars and Blaschke, Terrence, "Adherence to Medication", New England Journal of Medicine 2005; 353:487-97, Aug. 4, 2005.

Super-Resolution, Wikipedia, (Oct. 5, 2010) (4 pages).

University of Texas, GuideView, Mar. 15, 2007, http://www.sahs.uth.tmc.edu/MSriram/GuideView, (3 pages).

Valin, et al. "Video Surveillance of Medication intake", Int. Conf. of the IEEE Engineering in Medicine and Biology Society, New York City, USA, Aug. 2006.

Wang et al. "Recent Developments in human motion analysis." Pattern Recognition 36 (220) 585-601 (Nov. 2001).

Whitecup, Morris S., "2008 Patient Adherence Update: New Approaches for Success", www.guideline.com , The Trend Report Series, (Oct. 1, 2008) (17 pages).

* cited by examiner

METHOD AND APPARATUS FOR EMOTIONAL BEHAVIOR THERAPY

FIELD

This invention relates generally to encouragement of a change in the mood of a user, and more particularly to the encouragement of smiling or other mood change by a user to improve their mood and overall demeanor. The invention may also improve the mood and outcome of patients suffering from depression or any other situation in which a mood improvement may be beneficial. The invention may also engage a user and encourage an emotional response to consumption of a consumer product, ingestion of a medication or the like. Through continued use of the system, it may also improve the mood or emotion of a person on an ongoing basis

BACKGROUND

Recent research has found that encouragement of smiling on the part of an individual, even involuntarily smiling not in response to a happy event, may have a beneficial effect on the overall mood of the individual. The following references include descriptions background material regarding this phenomenon. http://www.psychologytoday.com/blog/isnt-what-i-expected/201207/try-some-smile-therapy describes that when a person is forced to smile, the perceive things as funnier, and that smiling can positively affect the mood of the person. http://smiletherapy.com/ suggest a method for setting an alarm, and smiling for one minute when the alarm sounds. http://www.anxietyguru.net/how-smiling-can-help-your-anxiety/ postulates that smiling can help one with their anxiety. http://lifeisnowblog.blogspot.fr/2009/06/faking-it-smile-therapy.html describes how happy behaviors, such as smiling, can foster happy feelings. While these sources describe the benefit of smiling, and one even suggests setting an alarm to provide a time to smile, there are no methods or apparatuses provided that provide a live feedback mechanism to monitor the benefits of smile or other emotional therapy to aid in performing and managing such therapy. There is further no interactive feedback system that monitors and encourages quality of smile therapy.

Thus, while these articles describe a desire to have people smile, there is no method presented for accurately tracking and encouraging the following of a proper protocol for smiling. Furthermore, there is no more general system for tracking and encouraging positive mood changes, and negating negative ones. Finally, there is no system providing feedback based upon a determined level of mood changes and/or smiling, and encouraging different or changes to activity based upon this feedback. Therefore, it would be desirable to provide an apparatus that overcomes the drawbacks of the prior art.

SUMMARY

In accordance with one or more embodiments of the invention, an application or other computer program, coupled with a device, or available for installation on another device, such as a user's mobile device or the like, is provided that provides one or more prompts to aid a user through a sequence of steps associated with a smile therapy regimen. An alarm integrated into the application may be set to go off regularly to encourage the therapy, or may increase an amount of interactive mood training of a user based upon one or more requirements and based upon an analysis of their mood, and further in accordance with one or more self=reported scales. Furthermore, the application or other computer program preferably employs one or more facial recognition tools to monitor that a user is properly performing the smile therapy regimen, and to encourage or otherwise provide aid in correcting any deviations from a preferred set of steps associated with the smile therapy. Thus, one or more question sets may be provided, allowing the user to rank their mood or other psychological or medical information. Various embodiments of the invention, as described below, may encourage or track the verification of adherence to a desired protocol, such as consumption of a product, following a medication protocol, ingestion of medication or other edible product, and then determine smiling and/or mood ratings in response. Particular states of a user may be determined based upon these inputs, and future input may be considered based upon a current state of the user.

In accordance with one or more embodiments of the present invention, continued training of emotions may prompt the emotions to be engrained in the patient. The present system may be more effective than medication in changing or training mood states for a patient. More intense moods may warrant greater use of the system and a mood scale may be assigned and tracked to a patient. Intervention may also be encouraged in the event that mood declines or does not increase over time.

In U.S. patent application Ser. No. 12/620,686, filed Nov. 18, 2009, titled Method and Apparatus for Verification of Medication Administration Adherence; currently abandoned; U.S. patent application Ser. No. 13/588,377, filed Jul. 26, 2012, titled Method and apparatus for Verification of Medication Adherence, currently pending; U.S. patent application Ser. No. 12/646,383, filed Dec. 23, 2009, titled Method and Apparatus for Verification of Clinical Trial Adherence, currently abandoned; U.S. patent application Ser. No. 13/588,380, filed Jul. 26, 2012, titled Method and Apparatus for Verification of Clinical Trial Adherence, currently pending; U.S. patent application Ser. No. 12/646,603, filed Dec. 23, 2009, titled Method and Apparatus for Management of Clinical Trials, currently pending; U.S. patent application Ser. No. 12/728,721, filed Mar. 22, 2010, titled Apparatus and Method for Collection of Protocol Adherence Data, currently pending; U.S. Patent Application Ser. No. 61/331,872, filed May 6, 2010, titled Apparatus and Method for Recognition of Patient Activities when Obtaining Protocol Adherence Data, expired; U.S. patent application Ser. No. 12/815,037, filed Jun. 14, 2010, titled Apparatus and Method for Recognition of Patient Activities when Obtaining Protocol Adherence Data, currently pending; U.S. Patent Application Ser. No. 61/495,415, filed Jun. 10, 2011, titled Method and Apparatus for Monitoring Medication Adherence, currently pending; U.S. patent application Ser. No. 13/189,518, filed Jul. 24, 2011, titled Method and Apparatus for Monitoring Medication Adherence, currently pending; U.S. Patent Application Ser. No. 61/498,576, filed Jun. 19, 2011, titled Apparatus and Method for Recognition of Patient Activities, expired; U.S. patent application Ser. No. 13/235,387, filed Sep. 18, 2011, titled Method and Apparatus for Recognition of Patient Activities, currently pending; U.S. patent application Ser. No. 13/214,201, filed Aug. 21, 2011, titled Apparatus and Method for Determination of Medication Location, currently pending; U.S. patent application Ser. No. 13/216,099, filed Aug. 23, 2011, titled Direct Observation of Consumables, currently pending; and U.S. patent application Ser. No. 13/369,757, filed Feb. 9, 2012, titled Method and Apparatus for Encouraging Consumption of a Product, currently pending the contents of these applications being incorporated herein by reference, the inventors of the present invention have proposed a system and method that allow for complete control and verification of adherence to a prescribed medication protocol or machine or apparatus use in a clinical trial setting, including following one or more predetermined steps and preferably determining ingestion or other application of a medication or other consumable object, whether in a health care provider's care, or when self administered in a homecare situation by a patient.

These applications present the only medication management system that may determine whether a user is actually following a medication administration protocol, provide additional assistance to a user, starting with instructions, video instructions, and the like, and moving up to contact from a medication administrator, if it is determined that the user may need such assistance in any medical adherence situation, including clinical trial settings, home care settings, healthcare administration locations, such as nursing homes, clinics, hospitals and the like, and in clinical trial settings.

In accordance with one or more embodiments of the present invention, it is proposed that methods and systems, such as those described in the above-referenced applications, be employed for the proper monitoring of a user following a proposed smile therapy regimen. Therefore, in accordance with one or more embodiments of the present invention, a method, apparatus and computer program or other mobile application or the like is provided that facilitates information presentation to a patient indicative of following a smile therapy procedure, and information capture of proper performance of such a smile therapy procedure. This smile therapy procedure may be included as part of a medication administration procedure, or as a standalone therapy. Therefore, in accordance with the present invention, a video capture device or computer program or other mobile application may be provided, including a memory, for storing captured video and other user data, analyzing such captured data, and providing feedback to the user to encourage adherence with a smile therapy regimen. Data may be captured as to smiling, laughter, etc. or other indications of mood, such as crying, sadness, etc. Such captured data may be further transmitted to a remote location for further analysis, storage, additional uses, and the like. The device, or computer program or other mobile application running on a device further may receive information from a remote location and provide information to the user in accordance with the received data, in accordance with the present invention. In accordance with a preferred embodiment of the invention, an apparatus is provided comprising a video capture device, an audio capture device, memory for storing such captured data, a processor adapted to operate analysis software for analyzing the captured data, a transmitter for transmitting the captured data, or other versions of the data or analysis results to a remote location, for receiving data and further instructions or communication from the remote location, and a display for providing such data or further instructions to the user. Such apparatus may preferably interface with management software adapted to manage multiple users, and thereby providing a full monitoring and data collection procedure.

The novel combination of text, graphical, pictorial, and video presented in accordance with the present invention allows for the first confirmation of proper adherence to a smile therapy regimen, and further allows for interactive and real time encouragement of the user in order to properly perform smile therapy procedures. The present invention provides an apparatus method and computer program or application that presents a number of solutions. The apparatus, method and computer program or application preferably may provide step-by-step image and video instructions to the user on how to properly perform a smile therapy regimen, and may also ask one or more questions of the user to determine changes in mood or other states of the user. Such questions may request the user to rate various answers on one or more scales, and may further provide a branching logic to allow for a more in depth data collection, such as may be provided in accordance with one or more ePRO diary systems that are currently available.

A specific smile therapy regimen may be programmed into a calendar included in accordance with one or more embodiments of the invention to alert the user when particular steps of a smile therapy regimen should be performed and may provide clear video instruction or other prompting for properly performing the steps. These reminders minimize forgetfulness by the user and aid in proper performance and timing of any such smile therapy regimen. The calendar function may also allow for the monitoring of the emotional state of the user over time. Thus, through monitoring, one may provide alerts when the emotional state of the user appears to be declining or otherwise changing over a period of time. Any such change in mood (especially if a decline in happiness) may prompt further self-reported data to be requested by the system, such as asking mood related questions. Tome of responses (audio) and apparent energy levels (video) may also be employed to compare user mood over time.

Once an alert is provided by the apparatus of the invention and the patient has confirmed that they are ready to perform the smile therapy steps, the method, apparatus and computer program or other application is preferably adapted to record the performance of the smile therapy steps and confirm proper performance through the use of computer vision and/or activity recognition. The user may also be prompted to perform smile therapy after administering or ingesting a medication or other product or the like, such as a can of soda, beer, etc. The method, apparatus and computer program or other application records or otherwise visually analyzes the visual record of the patient actually performing the smile therapy regimen steps, using any of the above recognition methods, and further preferably including facial recognition, badge identification, or any other method for confirming the identity of the individual. The user smiling may also be published to one or more social networking sites along with an image or statement related to the product they were consuming or using either in image or video format. A real-time log for audit trails and further analysis is thereby created. Additional information may be captured using a brief questionnaire on the device which may help to highlight changes in mood of the user. Data from all the population can be captured and presented in an aggregated manner online in real-time, giving real-time data results at a population level.

Additional data may be collected related to a degree or level of smile, and thus may provide immediate feedback and encouragement in an interactive manner. Larger smiles may be interactively encouraged if the user is not smiling enough, or for any other reason. For example, the user may see a celebrity, friend, relative, etc. smiling. In response, the user may be encouraged to increase the size of their smile. In response the inventive system may further recognize this increased smile of the user, and may in turn increase the smile of the celebrity on the display. Escalating moods may ultimately result in laughter, improving moods in a manner as if the user were actually present with the celebrity. Any determined visual or audio cues may be determined and/or employed in order to encourage a smile level, perhaps even matching the size of a smile provided on a character on a display.

It is therefore contemplated that the apparatus in accordance with the present invention be applicable to general healthcare settings where a user might be encouraged to employ smile therapy in order to improve their mood, or otherwise improve the user's overall health. Such therapy may be provided as an alternative to, or in conjunction with more traditional antidepressants or other medication.

Furthermore, while the apparatus constructed in accordance with the application has been described as implementing a method and system similar to that described in one or more of the above pending US Patent Applications, it is intended that the apparatus be available as a standalone apparatus, for use and implementation in systems other than those described in accordance with this or other noted patent applications, and may similarly be provided as a mobile or other application for downloading or other use on a device already owned by a user, on a device purchased or otherwise provided specifically for this purpose, or on any other available user device.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangement of parts that are adapted to affect such steps, all as exemplified in the following detailed disclosure, and the scope of the invention will be indicated in the claims.

BRIEF DESCRIPTION OF THE DRAWINGS

For a more complete understanding of the invention, reference is made to the following description and accompanying drawings, in which.

DETAILED DESCRIPTION

Figure 1:
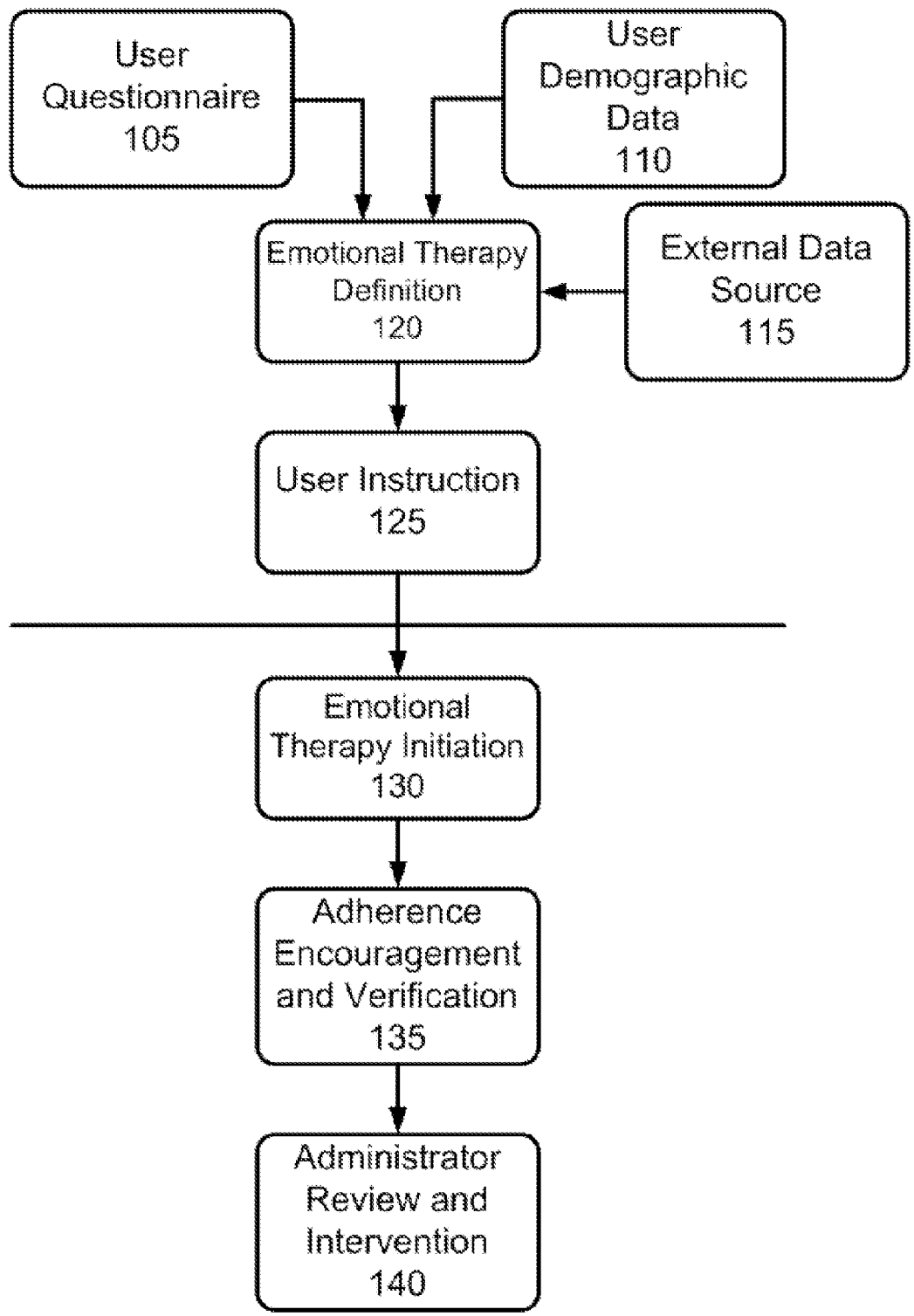
FIG. 1 is a flowchart diagram depicting an embodiment of the invention.

In accordance with one or more embodiments of the present invention, a system, process, computer program, downloadable or otherwise installable application, such as a mobile application on a mobile computing device, laptop, tablet computing device, or other appropriate computing device with a camera and a display or the like may be provided that provides instructions to a user for following a predetermined interactive and responsive smile or emotional therapy regimen, to aid in improved adherence to such a regimen, and give one or more administrators or other individuals possible overseeing a user a tangible and concrete manner in which to confirm adherence to the smile or emotional therapy or lack thereof and the ability to intervene early in the process to ensure that users intending to be employing such a regimen are properly following the regimen. The regimen may include determining levels of smile and/or laughter, and may also take into account various movements, audio responses and facial features. The systems (including device, computer program, and/or mobile or other application) and method of the invention provide for instructions to patients on the following or appropriate smile or other emotional therapy, and allow for analysis of use of the program by a supervisor on an individual, group or population level. The system and method of the invention further provide the ability to track emotions and moods of one or more users over time through the use of a simple set of questions or the like periodically asked of the user, thus allowing these survey results on mood and emotion to perhaps be correlated with adherence to the smile or other emotional therapy protocol to aid in determination of the effectiveness of the protocol, thus encouraging continued use, or perhaps suggesting one or more changes to the protocol (such as frequency, length of use, etc.

The system further may provide an automated interaction that is preferably prompted by one or more audio or video cues to encourage the user to smile and change their mood in a positive direction. Human intervention may be requested by the system if such improvement is not progressing, or proves impossible. Mood scores may further be assigned and used to compare states of a user over time. A system may also be included to allow for a social networking feature of the system, allowing for smile points or the like to be shared among groups, broadcast via a social networking site, or the like. In such a manner one or more individuals may be encouraged to smile through the interaction with friends, social media groups or the like. Finally, in addition to tracking smile therapy, the system may be employed to further track mood changes of a user based upon determined facial expressions, or other video or audio feedback captured from the user, and encourage changes thereof. In addition to smile points, the users may be allowed to publish themselves smiling in one or more images or short video segments to their social network. This broadcasting may take place in accordance with consumption or ingestion of a product, or using/doing some activity. Video segments may indicate that an action, such as taking a particular medication, has just taken place, ad that the mood of the user is good. The broadcasting may also take on an advertising role, allowing the display of a location where the medication was taken, the type of medication, etc. to be displayed. This may also comprise a restaurant if, for example, a food were just eaten, or the like. Or just drank a coke with a celebrity or great friend, etc. (who shared a laugh with me).

A level of smiling may be scaled and automatically presented to a friend. This could then be used as the interaction for the friend smiling. Thus, a user may take an image of themselves smiling, and send to a friend to further encourage smiling, perhaps with an encouraging message. This may be called a smilegram, slime message, smile chat, etc. After receiving such a message, a receiving user may press start, begin smiling in response, and get points for doing so. This process may be presented as interactive between the two participants and may continue back and forth, perhaps resulting in laughter. The images may be combined and posted to a social network site, or the like, indicating that the users had a good laugh together.

Referring first to FIG. 1, a data flow overview is shown. In accordance with the invention, a user may first be asked at step 105 to provide one or more pieces of information in a questionnaire type format. Such questions may be of any format, but in particular may be directed to determine a level of depression or other emotion issues that may be helped by smile therapy. Thus, the questions may be used, in part, to determine a particular therapy regimen to be employed. This therapy regimen may include one or more of alarm time for therapy, including number of times per day, duration, etc. Next, demographic or other user-related information may be determined at step 110, and used to group or otherwise categorize a user to determine once again details for a smile therapy regimen that may be most desirable for a user. Finally, at step 115, any other external data source, such as research papers, study findings and the like may further be input into the system to aid in defining an appropriate smile therapy regimen for the particular user. Thus, one or more of the noted sources may be used to define a smile therapy regimen at step 120. Additionally a user or third party may provide input and influence the prescribed smile or other emotional therapy. Once confirmed, a set of steps comprising the defined regimen are preferably determined and provided as one or more user instructions at step 125.

Such user instructions may include general instructions about the smile therapy regimen, or particular user real time feedback prompts with immediate feedback for the user to encourage proper regimen adherence. It is contemplated in accordance with one or more embodiments of the invention that such set of user instructions may be interactive, allowing a user to view additional information about such instructions as desired. These instructions may comprise written, audio or video instructions. Furthermore, it is contemplated in accordance with the invention that at various points during the instruction set, for example when a patient asks a particular type of question, or asks to receive additional information about a particular aspect of the therapy regimen, that the system may reach out and provide the user with additional, automated or personal help as necessary, if it is determined that such intervention may be helpful to the user. Thus, such a user may be assisted in properly performing the various steps of the defined (in step 120) smile therapy regimen so that various errors do not take place.

It is contemplated in accordance with one or more embodiments of the invention that a remote supervisor, friend, medical professional or other desired individual may be provided with a patient dashboard or other notification or alert system for managing regimes for one or more users of the application, device or the like employing the defined smile therapy. Such a dashboard allows the managing individual to monitor adherence of one or more users of the system to a prescribed smile therapy regimen, and to intervene when appropriate on a near real time basis, or later at a more desirable and convenient time. Such a dashboard may also provide the ability to monitor any number of users in a manner that will be described below, allow statistical analyses of user adherence and other patient reactions, provide links to information, including recorded activity sequences for one or more users, record and be made aware of any adverse events taking place during use, and generally allow the managing individual to monitor all users from a convenient single access point. Such information may also be provided a marketing data to aggregate smiles across a customer segment. This information may determine how happy particular customers are, may count a cumulative number of smiles in response to a particular image, brand, etc. Aggregated performance may be displayed on the dashboard, feedback being provided to all contributors, or to one or more groups of contributors.

In addition to monitoring by a particular individual, as noted above, a social media component may be employed, thus allowing social media groups to be formed around such a smile therapy, or for the user's existing social media group to provide further encouragement. Thus, upon performance of one or more smile therapies, notifications of such may be automatically posted to a user's social media page, broadcast to friends, or otherwise made available to others in a social media context. In such a manner, individual monitoring may not be necessary. Collective monitoring, contests for reaching a highest type of score or the like may be employed. Online smile events may be encouraged, perhaps providing sponsorship or charitable contributions in response to smiling. Smiling in response to a particular branding may earn discounts, rewards points, etc. Other incentive may be provided for properly taking medication, etc.

In such a manner, consistent usage of the system is preferably rewarded. Thus, such consistent usage may also be indicated in a social media context, and may also be provided as real time feedback to a user. Any number of thresholds may be employed in order to provide such feedback. In a social media context, it may be possible to allow for categorization of a particular user by percentage of how they are performing relative to their peers, thus potentially providing encouragement if they are doing well, and help if they are not. Group support may be a best way to provide help to potential users of the system, consistent positive interaction being a positive influence on individuals and their behavior.

Usability data may also be obtained from one or more users, and thus allow for the provision of feedback information to one or more moderators, and may indeed, allow for the modification of smile or emotional therapy details, such as timers, usage alarms, etc. Such usability data obtained on a large scale would further allow for the accumulation of various statistics that may be correlated with one or more questions that may be asked of the users, related to mood or other attributes of health, or anything else. Thus, outlook and the like may be determined, and various other metrics may be correlated, including but not limited to exercise, shopping trends, spending online, time on particular websites, time speaking with friends, time texting, etc. to allow for a more complete picture of such a user. This more complete picture may then be further used to determine any changes to various prescribed therapies for an individual or group.

It is contemplated in accordance with one or more embodiments of the present invention that a touch or other user friendly graphical user interface may be provided so that the user can easily manipulate any number of factors, such as timing of any reminders about smile therapy regimen instances and the like. Thus, within protocol parameters, the user may be able to modify one or more features of the therapy environment.

Referring to the lower portion of FIG. 1, the horizontal line indicates a time for user implementation of the smile therapy regimen. Thus, at step 130 smile therapy begins. Such initiation may be based upon a user action, or may be performed in accordance with a predetermined reminder or the like in accordance with the predetermined smile therapy regimen. Next, at step 135, in accordance with one or more embodiments of the invention, confirmation of patient adherence to the determine smile therapy is determined. While such confirmation may take a number of forms, in accordance with a preferred embodiment of the invention, a preferred method for such confirmation may include capturing a video sequence of the user actual performing the steps of the smile therapy regimen. In a further preferred method, such a sequence for such confirmation may include employing activity recognition, gesture recognition or other feature for determining whether a particular user facial movement meets a predefined movement sequence to be sure that the user is properly following the smile therapy regimen steps, and to what extent, such as by determining size of a smile, level of laughter and the like, as noted above. A system such as that described by any of the applications incorporated herein by reference may be employed. After such automatic or combination of automatic and manual adherence verification is performed, intervention may be performed by a managing individual. Additionally, such adherence review may be stored over time for a particular user, thus allowing for various trends to be determined, such as if a patient misses therapy and has a lower emotional state or worse mood, for example. Thus, in addition to allowing for immediate notice of success or failure of the smile therapy, an audit trail for tracking the benefits of the therapy may also be provided. Particular care pathways may be prompted, eventually leading to the system prompting the user to provide information related to non-use of the system for any particular reason.

Therefore, in accordance with the invention as set forth in FIG. 1, a method and system are provided in which user adherence to a determined smile therapy regimen can be reviewed, acutely for a particular instance, or over time to determine any changes in behavior or mood of a user. Because all aspects of such adherence are monitored preferably visually, and do not rely on user confirmation of smile therapy use, a true review of actual results of the therapy may be determined. Various collected demographic or other activity data may be correlated with such usage information in a manner as noted above in order to allow for determination of positive or negative activities, and their affect on mood and the like. Incentives, such as reward program points, or other desirable rewards may be provided to encourage good behavior, thus providing positive reinforcement where desirable.

Figure 2:
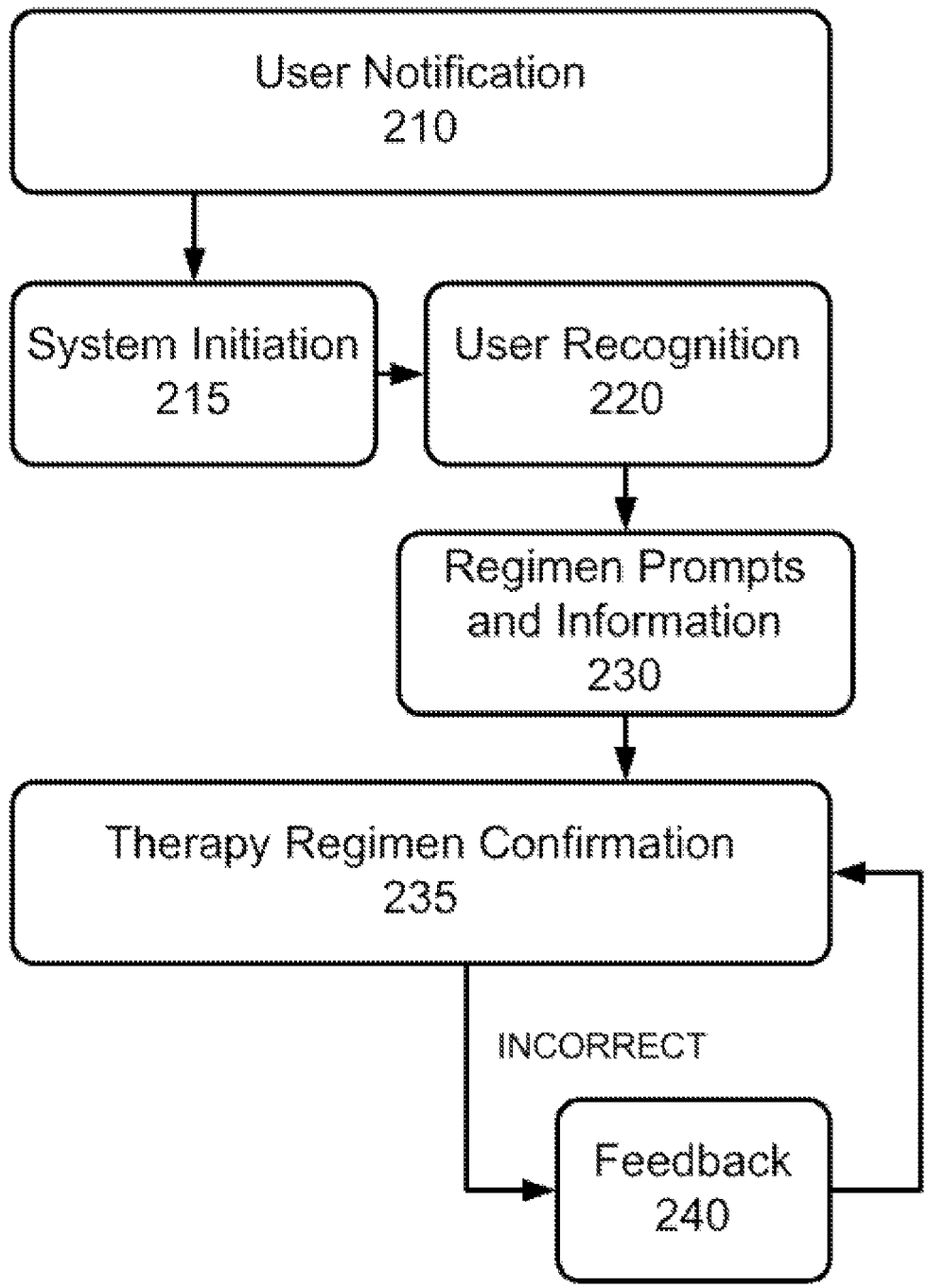
FIG. 2 is a flowchart diagram depicting further elements of an embodiment of the invention.

Referring next to FIG. 2, a user implementation of the method in accordance with the invention will be described. When a time for performing a particular smile therapy implementation is reached, a user may be provided a notification 210. This notification may be provided at a time indicated by a user, at a time defined by the smile therapy regimen, or not at all, allowing the user to start the system at any desired time. After notification, or in the absence of such notification, system initiation takes place at 215. In accordance with such system initiation, one or more users are preferably recognized by the system. Therefore, at step 320, a user recognition sequence may take place, although this step may easily be skipped, assuming that the user of a particular mobile device including a password, for example, is the intended user. In a preferred embodiment, such a user has a still or video image captured of their face, and facial recognition techniques are employed to confirm the identity of the user. Such capture may be performed by fixed camera, mobile camera, mobile communication device such as a cellular phone, or any other appropriate video or image capture device. Alternative recognition techniques, such as retinal, fingerprint, voice or other biometric measurements may be employed, in addition to a more common password query. Any other appropriate identification technique may be employed, and any unique individual identifiers may be obscured, as noted above, when the images are to be used as a more general report regarding adherence, rather than an individual patient response.

In step 230 user prompts and other instructions are provided to the user as to how to perform the various steps in accordance with the defined smile therapy. These instructions allow for a user to receive further information or instructions as necessary through asking the system for additional help. Especially in situations where an elaborate scheme may be required, it is contemplated that video samples and instructions may be provided to the user. Further, in accordance with the invention, for complicated administration procedures, it may be possible to set up a two way video conference employing traditional video conferencing, VOIP conferencing, traditional telephone conferencing, or any other appropriate communication system with an expert in such administration so that a user may receive live coaching regarding such smile therapy.

When following such instruction prompts, the actual act of smiling is preferably captured as a video sequence at step 235. Administration preferably includes one or more identifiable gestures as will be described below in accordance with one or more embodiments of the invention. Thus, a user may be provided with one or more prompts to properly perform a sequence of smile regimen steps. These prompts may include one or more images or animations of proper performance of each of the one or more steps, and thus the following of these sequences is used to determine compliance with a particular prescribed smile therapy regimen. If a determination is made that a particular step is being performed incorrectly, feedback may be provided to the user to perform the step properly at step 240. Thus, in such a manner, proper performance of the one or more steps of smile therapy may be confirmed.

Thus, in accordance with one or more embodiments of the invention, an emotion modification tool is provided in accordance with which through the automated confirmation of proper smile therapy administration, emotions and mood may be improved. One or more alarms may be provided to remind the user to begin the sequence of smile therapy steps. The system is operable to be used with any processor on any mobile or other device, and webcam or any camera. As is noted above, the prompts of the system provides a sequence of steps in accordance with a desired smile therapy regimen. In accordance with a preferred embodiment of the invention, such steps may include prompting the user to smile at a predetermined time. After such prompting, the system preferably employs computer vision, gesture recognition, facial expression recognition or the like to confirm that the user has smiled. In a preferred embodiment of the invention, the application may time the duration of one or more performed smile therapy steps, such as the number of times and the duration for which a user has smiled. Prompts, as noted above, may further indicate a time and number of times to perform the one or more smile therapy steps. Alternatively, a game like interface may be provided to time the number and duration of smiling performed by a user. Positive reinforcement may also be provided in accordance with determinations automatically made with the computer vision, gesture or other recognition of the activity of the user, such as smiling or the like. A video or other visual indication of a person, real, rotoscoped, cartoon or the like, may be provided in order to encourage further smiling and smiling bigger, perhaps, by the user. Questions may be asked of the user in order to correlate moods, emption, depression, and the like to use of the smile therapy. Levels of happiness, etc. may also be determined in accordance with one or more questions.

In accordance with an alternative embodiment of the invention, the above noted interactive feedback may be provided in accordance with a perceived or determined level of smiling. Thus, a visible scale may be provided to indicate a level or duration of smiling being performed by the user, thus encouraging a longer smile term, or a bigger or more visible smile. Such a scale may be provided as a face smiling back at the user, such as an animated, rotoscoped or manipulated live face. Achieving particular levels of smiling may prompt receipt of rewards in one or more reward programs, thus further encouraging following the determined smile therapy regimen.

As is noted above, any of these scales, determinations, questions and the like may be reported back to a centralized dashboard to allow for individual or cumulative determination for a single or multiple instances related to smile therapy use. Changes in mood may be employed to request further help from a family member, medical provider, friend or the like. Alternatively, changes in moods may be used to change a determined smile therapy regimen. Optimism and pessimism may be tested and determined and correlated with use of the smile therapy system, thus determining for a particular user whether such use is beneficial, and perhaps aiding in determining whether a different regimen may be more beneficial.

Such smile or mood therapy regimen tracker may be employed to combat anxiety by further incorporating a focusing component, thus asking a user to smile and/or focus on an image, sound or the like provided in accordance with the smile therapy regimen, perhaps in accordance with one or more of the initial question asked in accordance with FIG. 1. Further, humming a particular tone or the like may be prompted by the system, and determined in accordance with audio recognition or the like. Consistency of the humming and tone may be automatically determined, and further employed to determine adherence to the additional humming protocol, thus providing visual real-time interaction and positive reinforcement on how well the user hums. Real time feedback, in accordance with, or separate from, the feedback noted related to smiling may be provided to encourage proper humming. Such feedback may include other positive reinforcement, visual and audio feedback, points or other incentives awarded to the user or the like. Such humming or the like may be employed in conjunction with the above noted smile or emotional therapy, and is therefore available as an additional tool to be provided in accordance with an overall treatment therapy. Other focusing exercises may be employed, such as following a spot around a display with their finger, etc. in order to distract a user from their bad mood.

In accordance with the defined smile therapy regimen, smiling and possibly humming if desired, may be requested to be performed on a schedule in accordance with the determined smile therapy regimen. Reports based upon anxiety and use of the smile therapy system may be provided to one or more designated individuals. Alternatively, a user may be prompted to start the application for smile therapy upon feeling anxiety, thus measuring a level of anxiety a user may feel, and further determining the success or failure of the smile therapy regimen in controlling such anxiety. Such feedback may be provided to one or more designated individuals, such as a family member, treating physician or the like. Reminders to use the smile therapy system may be provided in the form of text messages, reminders, emails, or other alerts. The above-noted social media or other groups may also be notified of any such trends or information, thus providing a group support feel to the system, and perhaps further supporting a healing of the user.

Figure 3:
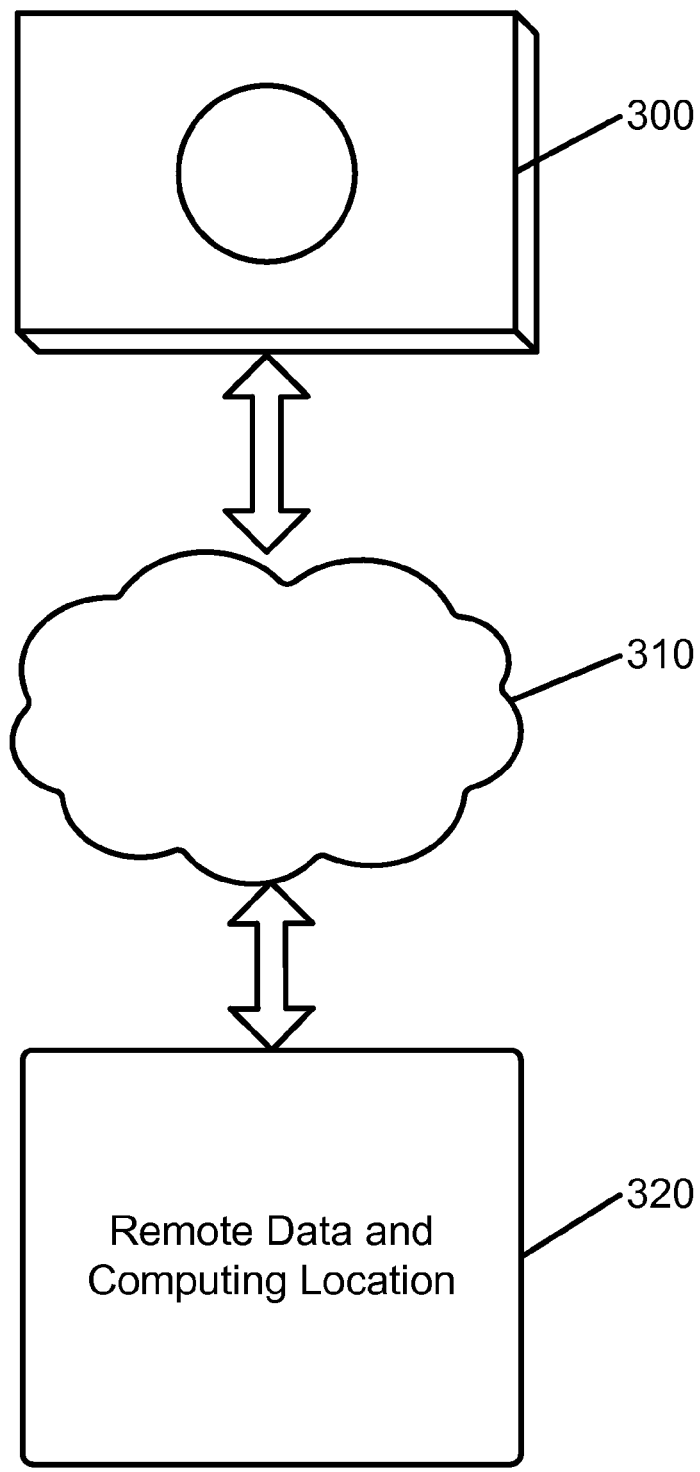
FIG. 3 is a block diagram depicting details of systems associated with an embodiment of the invention.

Referring next to FIG. 3, a remote information capture apparatus 100 is shown that may be employed in accordance with one or more embodiments of the invention. Such apparatus may comprise a specially designed apparatus, a standard hardware provided to a user, or a standard device in use by the user, with a smile therapy in accordance with the invention included thereon. Such apparatus is adapted to allow for the capture and processing of information in order to implement the system and method in accordance with the applications noted above and incorporated herein by reference. Such information capture apparatus 300 is placed in communication with a remote data and computing location 320 via a communication system 310, preferably the Internet or other communication system. Via communication system 310, information captured by apparatus 300 is transmitted to remote data and computing location 320, and analysis information or other instructions may be provided from remote data and computing location 320 to apparatus 300.

All communications in accordance with the invention are preferably encrypted or otherwise protected during transmission and storage at both local and remote mass storage location to meet any security issues and any regulations required for the storage and maintenance of medical and patient health care information.

Alternative embodiments of the invention may provide one or more of the following additional features. Rather than simply providing a video capture in a traditional sense, apparatus 100 may be provided with night vision, infrared vision, or other desired capture scheme. Apparatus 100 is also contemplated to be provided with a number of apparatus management features, including an ability to choose between color and black and white video storage and transmission, auto focus on a patient or the like, and including tracking of such an individual as they move about a room, the ability to strip any identifying information from transmitted video so that anonymity can be maintained, if desired. Apparatus 100 may include mechanisms to indicate a need for recharging, and include sleep modes for extending battery life. It is further contemplated that apparatus 100 may act as a monitoring device for a patient, and in a standby mode the apparatus may "listen" or "look" for sounds from the patient, including suggestions of depression, anxiety or the like. Automated responses may be provided in order to access patient status via integrated speakers or the like. The transmission system of apparatus 100 may then notify appropriate personnel. Thus, the portability and multiple use areas provide an additional benefit to the user of this apparatus.

In accordance with one or more further embodiments of the invention, the noted smile therapy system and method may be expanded to be applicable to all aspects of emotional therapy. Thus, the system and method may confirm sadness through facial expression, tears, stress in the face, twitching or shy movements or the like. Fear may be determined based upon similarly applicable characteristics that may be determined based upon audio and/or video capture, and analyzed in accordance with the described features of the invention. Different response care pathways may be provided based upon one or more determined emotional states and emotional trajectory over time.

By way of example only, and by no means an exhaustive list, one or more emotions for which the system may look may be selected from the group of: Fear, Anger, Guilt, Depression, Pride, Jealousy, Self-pity, Anxiety, Resentment, Envy, Frustration, Shame, Denial, Offended, Negative, Regret, Resentful, Sad, Worried, Grief, Love, Appreciation, Happiness, Hope, Enthusiasm, Vitality, Confidence, Gratitude, Patient, Trust, Vulnerable, Optimistic, Appreciative, Ashamed, Astonished, and the like.

Determination of any particular emotional state may result in the application of smile therapy as described herein, or may result in the user being asked a number of questions as noted above in order to determine one or more reasons for the user being in a particular emotional state. If the user is a consistent user of the system, upon determination of a particular emotional state, a determination may be made to determine whether the user has been in such an emotional state previously, and if so, reference what potential therapy may have been helpful in the past. For example, if a particular smile therapy was successful in aiding a particular user in the past, such a similar smile therapy may be provided for current use. Continued monitoring and questioning of the user may be employed to determine whether the therapy is working as in the past, or should be modified based upon updated user state or conditions. Customized interaction in the form of audio or video images may be triggered or offered based upon the determined emotional state of the user. If the user's mood changes, interactions may similarly change in order to continue a positive change in mood.

For example, if someone is not smiling or sad or a negative emotion is detection, then the system may provide an action to counter negative emotion. If positive emotion is identified, the user may be asked why they are feeling positive and information is used at a later date to provide positive feedback to that user when negative responses are identified. For example, if viewing a particular image or video improved the emotional state of a particular user, it is contemplated in accordance with the present invention to determine a need for such improvement in mood, and then preferably displaying the relevant video so that a similar emotional response may be evoked from the user at the current time. So the user can add content or information that they have classified as having a positive impact on their mood when they think about or otherwise interact with the content or information.

While scanning the face for emotional signposts, the system may also be adapted to recognize one or more warning signs of disease, such as changes in color of skin, lips or eyes over time, existence of bloodshot eyes, white rings about the eyes, drooping eyelids, twitches or the like. Combined with an emotional state determination on the part of the user, these signs may give greater insight into the possible caused of particular emotional states on the part of the user. Thus, once again, any such additional information may be employed to determine emotional state and appropriate smile therapy response in order to attempt to improve the mood of the user.

The system may be further employed in accordance with one of the medication administration monitoring system described in one or more of the applications incorporated herein by reference. Thus, in addition to monitoring medication administration, the apparatus may be employed to also incorporate features described herein to determine and track the emotional state of the user, and to report changes therein to a healthcare provider or other individual.

Further in accordance with one or more embodiments of the invention, a user who has been prescribed a smile therapy for depression or the like may be provided with an alarm to start the system or app, and then may further have their emotional state determined in accordance with any of the methods noted herein. One or more questions may also be provided to the user to correlate self reporting with the determined states. Thus, the user may be asked how they are feeling during one or more uses of the system. The user may be further asked to indicate a thing such as a video, thought, person, etc. That has recently made them happy. In the case of a video that is included on the device of the user, that video may be used in the future to improve the mood of the user.

During use of the system for performing therapy that includes smile therapy, the user may be instructed to perform a particular action such as smiling for a particular period of time. A countdown timer may also be provided. Once achieved, a bigger smile may be provided to show positive feedback to the user, or to encourage still more, larger smiles on the part of the user. After performing this increased (or initial) smile therapy the user may be further asked to rate their mood, the system capturing any self-reported improvement in mood. Positive reinforcement through audio of visual feedback, rewards, etc. may also be provided.

Subsequently, upon use of the therapy system, or when using one or more of the medication tracking systems noted above, recognition of a mood problem based upon facial characteristics may prompt the user to perform the smile or other emotional behavior therapy.

The system may also be employed in order to associate a positive mood of a user with a particular product. Thus, the user may be prompted to consume a particular product while being encouraged to smile. A larger smile may be encouraged once a smaller smile has been confirmed. Encouraged laughter may be further encouraged, all while consuming and/or holding a particular product. A drink, soda, beer food or the like may be such a product. An image of a celebrity or other person known to you may be employed. In this manner, good feelings and mood may be associated by the user with consumption of the product.

Therefore, in accordance with the invention, a method and apparatus are provided that allow for the automated confirmation of adherence to emotional behavior therapy, and for otherwise improving a mood of a user.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that this description is intended to cover all of the generic and specific features of the invention herein described and all statements of the scope of the invention which, as a matter of language, might be said to fall there between.

What is claimed:

1. A method of encouraging emotional behavior therapy, comprising:
    identifying a particular emotional behavior therapy prescription regimen to be performed by a user;
    determining by a processor one or more procedures for administering the particular emotional behavior therapy prescription regimen;
    identifying by the processor one or more video activity sequences associated with the one or more procedures;
    in response to determining the one or more procedures for administering the particular emotional behavior therapy prescription regimen, providing on a display associated with the processor one or more instruction prompts associated with the one or more procedures for administering the particular emotional behavior therapy prescription regimen;
    capturing video activity sequences, by a camera associated with the processor, of actual administration of the emotional behavior therapy prescription regimen following the display of the one or more instruction prompts;
    storing the captured video activity sequences to a non-transitory computer readable storage medium associated with the processor;
    comparing by the processor the stored video activity sequences to the identified one or more video activity sequences to determine differences therebetween; and
    providing on the display an updated one or more further instruction prompts associated with the particular emotional behavior therapy prescription regimen in response to the one or more determined differences.

2. The method of claim 1, wherein the emotional behavior therapy prescription regimen comprises smile therapy.

3. The method of claim 2, wherein one or more of the procedures comprise smiling for a predetermined period of time.

4. The method of claim 2, wherein one or more of the one or more instruction prompts comprise an encouragement to smile.

5. The method of claim 4, wherein the one or more of the one or more instruction prompts comprise a face with a simulated smile.

6. The method of claim 4, wherein one or more of the one or more further instruction prompts comprise a request for a change in the action currently being performed by the user.

7. The method of claim 6, wherein the one or more of the one or more further instruction prompts comprise real time interactive feedback to the user.

8. The method of claim 1, comprising:
capturing video activity sequences by the camera, of multiple instances of actual administration of the emotional behavior therapy prescription regimen;
transmitting the captured video activity sequences of the multiple instances of actual administration of the emotional behavior therapy prescription regimen to a remote server location by a transmission system;
further analyzing the captured video activity sequences by an additional processor associated with the remote server location, wherein further analyzing comprises comparing each of the captured video activity sequences to the identified video activity sequences to determine differences therebetween; and
providing an analysis of adherence to the particular emotional therapy prescription regimen based on the determination of the differences.

9. The method of claim 8, further comprising modifying one or more of the one or more procedures in accordance with the provided analysis.

10. A system for encouraging emotional behavior therapy, comprising:
an input device operable to receive information from one or more prescribing individuals defining a particular emotional behavior therapy prescription regimen to be performed by a user;
a processor;
a storage device associated with the input device and the processor, wherein the storage device is operable to store a set of instruction prompts generated by the processor in response to the information received by the input device, wherein the set of instruction prompts is associated with one or more procedures for administering the particular emotional behavior therapy prescription regimen, and wherein the storage device is operable to store one or more identified video activity sequences associated with the set of instruction prompts;
a display associated with the processor, wherein the processor is operable to output to the display the set of instruction prompts;
a camera operable to capture video activity sequences of actual administration of the particular emotional behavior therapy prescription regimen by the user in response to the set of instruction prompts being displayed, wherein the storage device is operable to store the captured video sequences, wherein
the processor locally associated with the video capture device for is further operable to
compare the stored video activity sequences to the identified video activity sequences to determine differences therebetween,
to automatically determine whether administration of the particular emotional behavior therapy prescription regimen has failed, and
to output to the display an updated one or more further instruction prompts associated with the particular emotional behavior therapy prescription regimen in response to determining that the administration has failed.

11. The system of claim 10, wherein the particular emotional behavior therapy prescription regimen comprises smile therapy.

12. The system of claim 11, wherein one or more of the procedures comprise smiling for a predetermined period of time.

13. The system of claim 11, wherein one or more of the one or more instruction prompts comprise an encouragement to smile.

14. The system of claim 13, wherein the one or more of the one or more instruction prompts comprise a face with a simulated smile.

15. The system of claim 13, wherein one or more of the one or more further instruction prompts comprise a request for a change in the action currently being performed by the user.

16. The system of claim 15, wherein the one or more of the one or more further instruction prompts comprise real time interactive feedback to the user.

17. A system for improving an emotional state of a user, comprising:
a video capture device operable to capture one or more video sequences of the face of a user;
a processor operable to
analyze the one or more captured video sequences to determine a current emotional state of the user, and
define an emotional behavior therapy prescription regimen in response to the determined current emotional state;
a display associated with the video capture device, wherein the processor is operable to output to the display one or more instruction prompts encouraging the user to properly follow the defined emotional behavior therapy prescription regimen,
wherein the video capture device is further operable to capture one or more video activity sequences of actual administration of the defined emotional behavior therapy prescription regimen by the user following the one or more instruction prompts, and wherein the processor is operable to store the captured video activity sequences to a storage medium locally associated with the video capture device,
wherein the processor is further operable to compare the stored video activity sequences to the defined emotional behavior therapy prescription regimen to determine differences therebetween, and
wherein the processor is operable to output to the display an updated one or more further instruction prompts associated with the emotional behavior therapy prescription regimen in response to one or more determined differences.

18. The system of claim 17, wherein the processor is further operable to output to the display a set of questions to the user in response to the determined current emotional state of the user.

19. The system of claim 17, wherein defining the emotional behavior therapy prescription regimen in response to the determined current emotional state comprises selecting a previous emotional behavior therapy prescription regimen that was successful in assisting the user when the user's the processor emotional state was last similar to the determined current emotional state.

20. The system of claim 17, wherein the emotional behavior therapy prescription regimen comprises smile therapy.

* * * * *